(12) United States Patent
Chinchoy

(10) Patent No.: US 7,610,088 B2
(45) Date of Patent: Oct. 27, 2009

(54) METHOD AND APPARATUS FOR ASSESSING LEFT VENTRICULAR FUNCTION AND OPTIMIZING CARDIAC PACING INTERVALS BASED ON LEFT VENTRICULAR WALL MOTION

(75) Inventor: Edward Chinchoy, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 496 days.

(21) Appl. No.: 10/376,981

(22) Filed: Feb. 28, 2003

(65) Prior Publication Data

US 2004/0172078 A1 Sep. 2, 2004

(51) Int. Cl.
*A61N 1/365* (2006.01)
(52) U.S. Cl. .................................................. 607/17
(58) Field of Classification Search ............... 607/4–28
See application file for complete search history.

(56) References Cited

U.S. PATENT DOCUMENTS

| | | | | |
|---|---|---|---|---|
| 5,109,842 A | * | 5/1992 | Adinolfi | 607/2 |
| 5,304,208 A | | 4/1994 | Inguaggiato et al. | |
| 5,423,883 A | | 6/1995 | Helland | |
| 5,549,650 A | * | 8/1996 | Bornzin et al. | 607/24 |
| 5,549,652 A | | 8/1996 | McClure et al. | |
| 5,628,777 A | * | 5/1997 | Moberg et al. | 607/122 |
| 5,836,987 A | | 11/1998 | Baumann et al. | |
| 5,991,661 A | * | 11/1999 | Park et al. | 607/19 |
| 6,044,299 A | | 3/2000 | Nilsson | |
| 6,278,894 B1 | | 8/2001 | Salo et al. | |
| 6,285,906 B1 | | 9/2001 | Ben-Haim et al. | |
| 6,885,889 B2 | * | 4/2005 | Chinchoy | 607/9 |
| 2001/0031993 A1 | * | 10/2001 | Salo et al. | 607/9 |
| 2003/0105496 A1 | * | 6/2003 | Yu et al. | 607/17 |
| 2004/0015081 A1 | * | 1/2004 | Kramer et al. | 600/439 |
| 2004/0019365 A1 | * | 1/2004 | Ding et al. | 607/17 |
| 2004/0024421 A1 | * | 2/2004 | Ideker et al. | 607/9 |

FOREIGN PATENT DOCUMENTS

| | | |
|---|---|---|
| EP | 0515319 B1 | 8/1997 |
| WO | WO 95/03086 | 2/1995 |

* cited by examiner

*Primary Examiner*—Scott M Getzow
(74) *Attorney, Agent, or Firm*—Stephen W. Bauer

(57) ABSTRACT

A system and method for monitoring left ventricular (LV) lateral wall motion and for optimizing cardiac pacing intervals based on left ventricular lateral wall motion is provided. The system includes an implantable or external cardiac stimulation device in association with a set of leads including a left ventricular epicardial or coronary sinus lead equipped with a motion sensor electromechanically coupled to the lateral wall of the left ventricle. The device receives and processes wall motion sensor signals to determine a signal characteristic indicative of systolic LV lateral wall motion or acceleration. An automatic pacing interval optimization method evaluates the LV lateral wall motion during varying pacing interval settings, including atrial-ventricular intervals and inter-ventricular intervals and selects the pacing interval setting(s) that correspond to LV lateral wall motion associated with improved cardiac synchrony and hemodynamic performance.

21 Claims, 9 Drawing Sheets

METHOD AND APPARATUS FOR ASSESSING LEFT VENTRICULAR FUNCTION AND OPTIMIZING CARDIAC PACING INTERVALS BASED ON LEFT VENTRICULAR WALL MOTION

FIELD OF THE INVENTION

The present invention relates generally to implantable medical devices for monitoring or treating a cardiac abnormalities and more particularly to a device and method for delivering cardiac pacing impulses at inter-chamber intervals that are optimized based on left ventricular wall motion monitoring.

BACKGROUND OF THE INVENTION

Evaluation of left ventricular function is of interest for both diagnostic and therapeutic applications. During normal cardiac function, the left atrium, the left ventricle, and the right ventricle observe consistent time-dependent relationships during the systolic (contractile) phase and the diastolic (relaxation) phase of the cardiac cycle. During cardiac dysfunction associated with pathological conditions or following cardiac-related surgical procedures, these time-dependent mechanical relationships are often altered. This alteration, when combined with the effects of weakened cardiac muscles, reduces the ability of the ventricle to generate contractile strength resulting in hemodynamic insufficiency.

Ventricular dyssynchrony following coronary artery bypass graft (CABG) surgery is a problem encountered relatively often, requiring post-operative temporary pacing. Atrio-biventricular pacing has been found to improve post-operative hemodynamics following such procedures.

Ventricular resynchronization therapy has been clinically demonstrated to improve indices of cardiac function in patients suffering from congestive heart failure. Cardiac pacing may be applied to one or both ventricles or multiple heart chambers, including one or both atria, to improve cardiac chamber coordination, which in turn is thought to improve cardiac output and pumping efficiency. Clinical follow-up of patients undergoing resynchronization therapy has shown improvements in hemodynamic measures of cardiac function, left ventricular volumes, and wall motion. However, not all patients respond favorably to cardiac resynchronization therapy. Physicians are challenged in selecting patients that will benefit and in selecting the optimal pacing intervals applied to resynchronize the heart chamber contractions.

Selection of atrial-ventricular (A-V) and inter-ventricular (V-V) pacing intervals may be based on echocardiographic studies performed to determine the settings resulting in the best hemodynamic response. However, this approach provides only an open-loop method. After evaluating the hemodynamic effect of varying combinations of pacing intervals, a physician must manually select and program the desired parameters and assume that the patient's device optimal settings remain unchanged until a subsequent re-optimization visit. Automated methods for selecting pacing intervals during multi-chamber pacing have been proposed. A four-chamber pacing system that includes impedance sensing for determining the timing of right heart valve closure or right ventricular contraction and adjusting the timing of delivery of left ventricular pace pulses is generally disclosed in U.S. Pat. No. 6,223,082 issued to Bakels, et al., incorporated herein by reference in its entirety. Programmable coupling intervals selected so as to provide optimal hemodynamic benefit to the patient in an implantable multichamber cardiac stimulation device are generally disclosed in U.S. Pat. No. 6,473,645 issued to Levine, incorporated herein by reference in its entirety.

Doppler tissue imaging has been used clinically to evaluate myocardial shortening rates and strength of contraction. This rate of contraction has been investigated as a determinant of clinical health of the ventricle. Doppler tissue imaging has also been used to investigate coordination between septal and lateral wall motion for predicting which patients are likely to benefit from cardiac resynchronization therapy. Evidence suggests patient response is dependent on the degree of ventricular synchrony before and after therapy. Doppler tissue imaging studies have shown that the left ventricular mid to mid-basal segments show the greatest improvement in shortening following cardiac resynchronization therapy. Detection and monitoring of left ventricular wall motion, therefore, would be useful in optimizing cardiac resynchronization therapy.

Implantable sensors for monitoring heart wall motion have been described. A sensor implanted in the heart mass for monitoring heart function by monitoring the momentum or velocity of the heart mass is generally disclosed in U.S. Pat. No. 5,454,838 issued to Vallana et al. A catheter for insertion into the ventricle for monitoring cardiac contractility having an acceleration transducer at or proximate the catheter tip is generally disclosed in U.S. Pat. No. 6,077,236 issued to Cunningham. Implantable leads incorporating accelerometer-based cardiac wall transducers are generally disclosed in U.S. Pat. No. 5,628,777 issued to Moberg, et al. A device for sensing natural heart acceleration is generally disclosed in U.S. Pat. No. 5,693,075, issued to Plicchi, et al. A system for myocardial tensiometery including a tensiometric element disposed at a location subject to bending due to cardiac contractions is generally disclosed in U.S. Pat. No. 5,261,418 issued to Ferek-Petric et al. All of the above-cited patents are hereby incorporated herein by reference in their entirety.

Detection of peak endocardial wall motion in the apex of the right ventricle for optimizing A-V intervals has been validated clinically. A system and method for using cardiac wall motion sensor signals to provide hemodynamically optimal values for heart rate and AV interval are generally disclosed in U.S. Pat. No. 5,549,650 issued to Bornzin, et al., incorporated herein by reference in its entirety. A cardiac stimulating system designed to automatically optimize both the pacing mode and one or more pacing cycle parameters in a way that results in optimization of a cardiac performance parameter, including for example heart accelerations, is generally disclosed in U.S. Pat. No. 5,540,727, issued to Tockman, et al.

A need remains, however, for providing a device and method for monitoring left ventricular wall motion and for selecting optimal cardiac pacing intervals that produce the greatest improvement in left ventricular wall motion during multi-chamber or biventricular pacing delivered to improve heart chamber synchronization, chronically or acutely. Improved left ventricular wall motion is expected to reflect an improvement in cardiac chamber synchrony and generally result in a net improvement in cardiac efficiency.

SUMMARY OF THE INVENTION

The present invention provides a method and apparatus for assessing left ventricular function and optimizing cardiac pacing intervals based on detection of left ventricular wall motion. In one embodiment, the present invention is realized in a cardiac resynchronization system that includes an implantable multi-chamber pulse generator and associated lead system wherein a left ventricular coronary sinus lead or left ventricular epicardial lead is provided with a sensor for detecting left ventricular wall motion. In an alternative embodiment, a temporary, external pulse generator is coupled to temporary pacing leads including a left ventricular temporary pacing lead equipped with a wall motion sensor. For each embodiment of the present invention, in addition to the pulse generator appropriate defibrillator circuitry may be employed in electrical communication to suitable In a preferred embodiment, the wall motion sensor is an accelerometer, which may be a uniaxial, biaxial, or triaxial accelerometer. Alternatively, the wall motion sensor may be provided as other types of piezoelectric sensors, optical sensors, Hall-effect type sensors, capacitive, resistive, inductive or any other type of sensor capable of generating a signal proportional to left-ventricular free wall motion or acceleration. A left ventricular wall motion sensor is preferably placed in or proximate the mid- or mid-basal left ventricular free wall segments.

The implantable or external pulse generator receives and processes the wall motion sensor signal during an automated testing routine, which includes application of varying resynchronization pacing intervals, including atrial-ventricular and/or ventricular-ventricular intervals. Signal processing is performed to time-average the wall motion signal and derive averaged signal parameters as indices of left ventricular free wall motion or acceleration. The pacing intervals producing the greatest improvement in left ventricular wall motion, based on the wall motion sensor data, can be automatically selected for delivering cardiac resynchronization therapy.

DETAILED DESCRIPTION OF THE INVENTION

As indicated above, the present invention is directed toward providing a method and apparatus for evaluating left ventricular function and selecting cardiac pacing intervals for the purposes of restoring normal ventricular synchrony based on monitoring left ventricular free wall motion. The present invention is useful in optimizing atrial-ventricular and inter-ventricular pacing intervals during chronic resynchronization therapy used for treating heart failure. The present invention is also useful in selecting pacing parameters used during temporary pacing applied for treating post-operative ventricular dyssynchrony. As such, the present invention may be embodied in an implantable cardiac pacing system including a dual chamber or multichamber pacemaker and associated set of leads. Alternatively, the present invention may be embodied in a temporary pacing system including an external pacing device with associated temporary pacing leads.

Figure 1A:
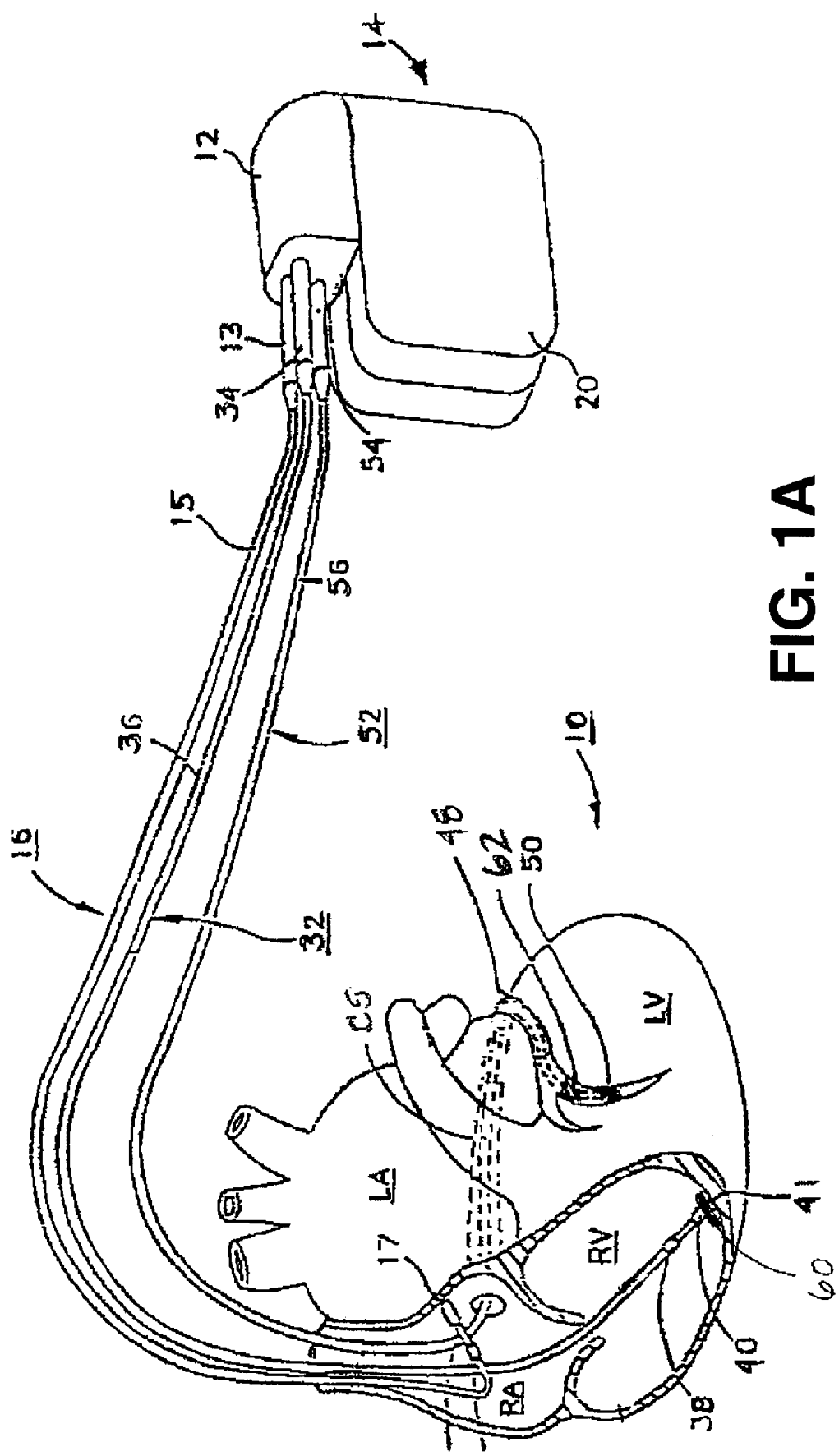
FIG. 1A depicts an exemplary implantable, multi-chamber cardiac pacemaker coupled to a patient's heart via transvenous endocardial leads.

FIG. 1A depicts an exemplary implantable, multi-chamber cardiac pacemaker 14 in which the present invention may be implemented. The multi-chamber pacemaker 14 is provided for restoring ventricular synchrony by delivering pacing pulses to one or more heart chambers as needed to control the heart activation sequence. The pacemaker 14 is shown in communication with a patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) extending from the opening in the right atrium laterally around the atria to form the great cardiac vein 48, which branches to form inferior cardiac veins.

The pacemaker 14, also referred to herein as the "implantable pulse generator" or "IPG," is implanted subcutaneously in a patient's body between the skin and the ribs. Three transvenousendocardial leads 16, 32 and 52 connect the IPG 14 with the RA, the RV and the LV, respectively. Each lead has at least one electrical conductor and pace/sense electrode. A remote indifferent can electrode 20 is formed as part of the outer surface of the housing of the IPG 14. The pace/sense electrodes and the remote indifferent can electrode 20 can be selectively employed to provide a number of unipolar and bipolar pace/sense electrode combinations for pacing and sensing functions.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21 provided for achieving RA pacing and sensing of RA electrogram (EGM) signals.

Bipolar, endocardial RV lead 32 is passed through the RA into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38 provided for RV pacing and sensing of RV EGM signals. RV lead 32 may optionally include a RV wall motion sensor 60. RV wall motion sensor 60 may be positioned into or proximate the RV apex for detecting motion or acceleration of the RV apical region. Implantation of an acceleration sensor in the right ventricle is generally disclosed in the above-cited U.S. Pat. No. 5,693,075 issued to Plicchi, et al.

In this illustrated embodiment, a unipolar, endocardial LV CS lead 52 is passed through the RA, into the CS and further into a cardiac vein to extend the distal LV CS pace/sense electrode 50 alongside the LV chamber to achieve LV pacing and sensing of LV EGM signals. The LV CS lead 52 is coupled at the proximal end connector 54 fitting into a bore of IPG connector block 12. A small diameter unipolar lead body 56 is selected in order to lodge the distal LV CS pace/sense electrode 50 deeply in a cardiac vein branching from the great cardiac vein 48.

In accordance with the present invention, the coronary sinus lead 52 is provided with a sensor 62 capable of generating a signal proportional to the motion of the left ventricular free wall. Sensor 62 is preferably embodied as a uniaxial, biaxial, or triaxial accelerometer contained in a capsule of a relatively small size and diameter such that it may be included in a coronary sinus lead without substantially increasing the lead diameter or impairing the ability to steer the lead to a left ventricular pacing and sensing site. Radial information may not be as valuable in assessing LV wall motion and optimizing pacing intervals as longitudinal information, therefore, a uniaxial accelerometer may be adequate for these purposes. Sensor 62 may alternatively be provided as another type of sensor such as an optical, acoustical, or Hall effect sensor or a sensor having piezoelectric, inductive, capacitive, resistive, or other elements which produce a variable signal proportional to left ventricular wall motion or acceleration. Sensor 62 is preferably located on CS lead 52 such that when CS lead 52 is positioned for LV pacing and sensing, sensor 62 is located approximately over the left ventricular free wall mid-lateral to mid-basal segments. The depicted positions of the leads and electrodes shown in FIG. 1A in or about the right and left heart chambers are approximate and merely exemplary. For example, a left ventricular wall motion sensor 62 may alternatively be located on CS lead 52 such that sensor 62 is positioned in the coronary sinus, in the great cardiac vein, or in any accessible inferior cardiac vein. Furthermore, it is recognized that alternative leads and pace/sense electrodes that are adapted for placement at pacing or sensing sites on or in or relative to the RA, LA, RV and LV may be used in conjunction with the present invention.

In a four chamber embodiment, LV CS lead 52 could bear a proximal LA CS pace/sense electrode positioned along the lead body to lie in the larger diameter coronary sinus adjacent the LA for use in pacing the LA or sensing LA EGM signals. In that case, the lead body 56 would encase an insulated lead conductor extending proximally from the more proximal LA CS pace/sense electrode(s) and terminating in a bipolar connector 54.

Figure 1B:
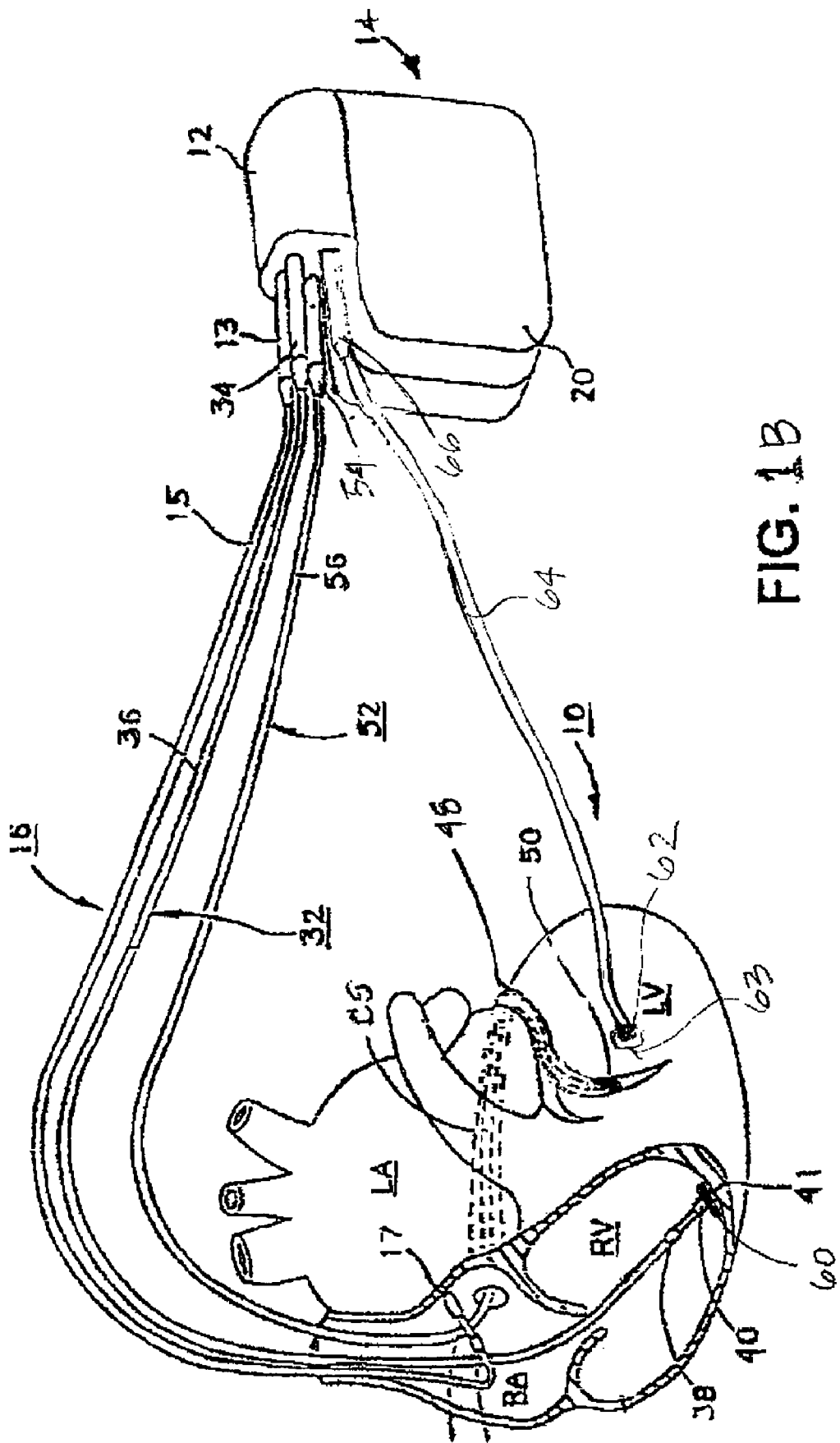
FIG. 1B depicts an exemplary implantable, multi-chamber cardiac pacemaker coupled to a patient's heart via transvenous endocardial leads and an additional left ventricular epicardial lead equipped with a wall motion sensor.

FIG. 1B depicts an exemplary implantable, multi-chamber cardiac pacemaker coupled to a patient's heart via transvenous endocardial leads and an additional left ventricular epicardial lead equipped with wall motion sensor 62. Patients may already be implanted with a transvenous lead system that includes a coronary sinus lead 52 that is not equipped with a wall motion sensor. Such patients may benefit from the placement of an epicardial lead 64 equipped with wall motion sensor 62 coupled to IPG 14 via a connector 66 so as to provide an LV wall motion signal for use in a closed-loop feedback system for providing resynchronization therapy at optimal pacing intervals.

Epicardial lead 64 is provided with a fixation member 63 which may serve additionally as a pacing and/or sensing electrode. In some cases, an epicardial lead may be preferred over a coronary sinus lead due to the difficulty in advancing a coronary sinus lead into a cardiac vein over the LV free wall. Placement of a coronary sinus lead can be a cumbersome task due to the tortuosity of the cardiac veins. Therefore, it may be desirable, at least in some patients, to provide an epicardial lead that can be positioned on the LV lateral wall for pacing, EGM sensing and wall motion monitoring, eliminating the need for a coronary sinus lead. Alternatively, it may be desirable to deploy a small diameter coronary sinus lead for LV pacing and EGM sensing with a separate LV epicardial lead positioned for sensing LV lateral wall motion.

The embodiment generally shown in FIG. 1B is particularly advantageous for use in selecting resynchronization therapy pacing sites. With epicardial lead 64 fixed at a desired location for assessing LV wall motion, the effect of pacing at different locations in one or more heart chambers can be evaluated by deploying the transvenous pacing leads 16, 32 and 52 to different locations. In particular, coronary sinus lead 52 may be advanced to different locations until an optimal location is identified based on analysis of the signal from LV wall motion sensor 62. By providing wall motion sensor 62 on a separate, epicardial lead 64, the position of pacing electrode 50, provided on coronary sinus lead 52, may be adjusted independently of sensor 62. If the position of pacing electrode 50 needs adjusting, wall motion sensor 62 may remain fixed at a desired LV lateral wall location thereby allowing comparisons to be made between measurements repeated at the same location for different pacing intervals and/or pacing sites.

Figure 2:
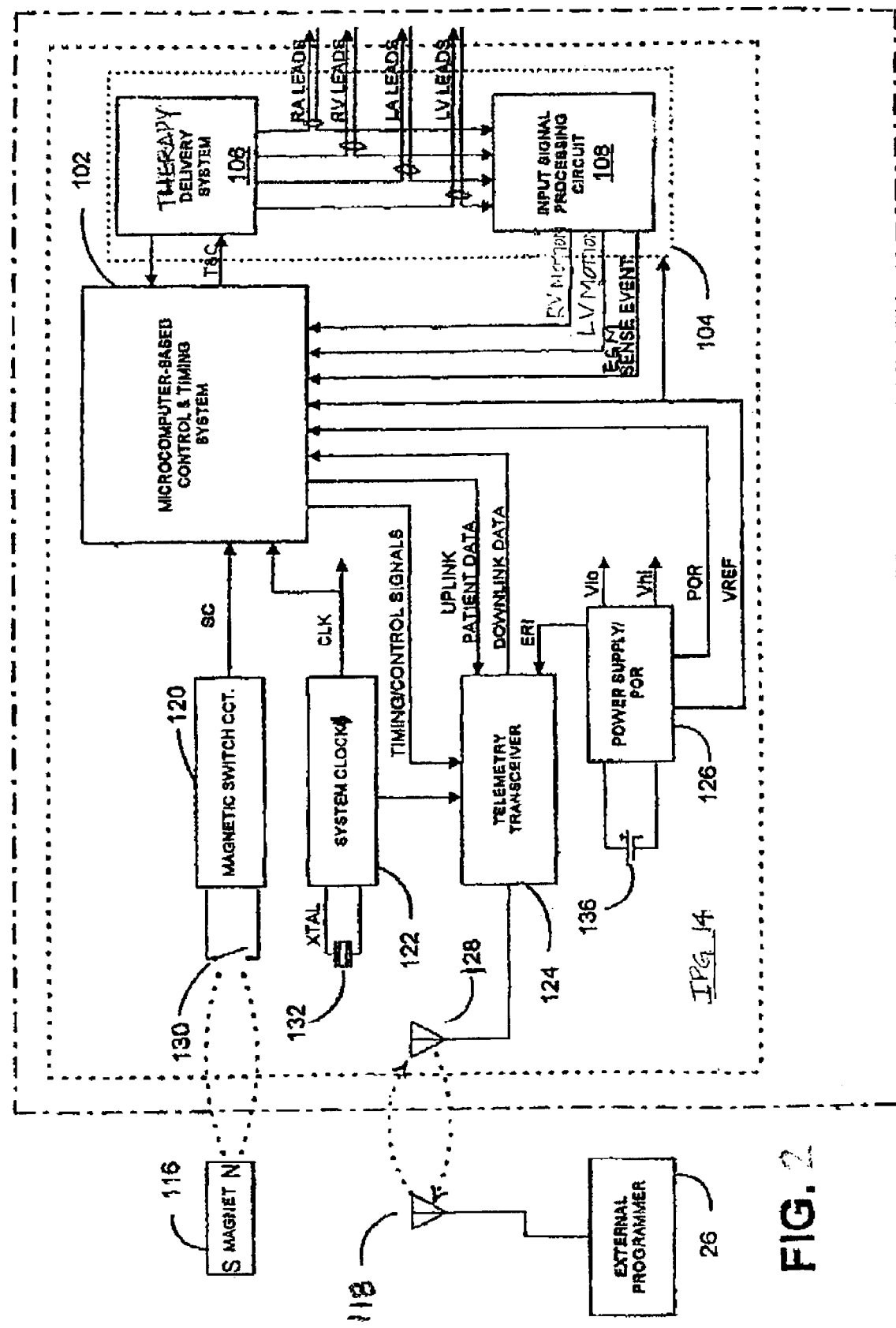
FIG. 2 is a schematic block diagram of the multi-chamber pacemaker of FIG. 1A capable of delivering a resynchronization therapy and processing left ventricular wall motion sensor signal input.

FIG. 2 is a schematic block diagram of an exemplary multi-chamber IPG 14, such as that shown in FIG. 1A or 1B, that provides delivery of a resynchronization therapy and is capable of processing left ventricular wall motion sensor signal input. The IPG 14 is preferably a microprocessor-based device. Accordingly, microprocessor-based control and timing system 102, which varies in sophistication and complexity depending upon the type and functional features incorporated therein, controls the functions of IPG 14 by executing firmware and programmed software algorithms stored in associated RAM and ROM. Control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner known in the art. It will also be understood that control and timing functions of IPG 14 can be accomplished with dedicated circuit hardware or state machine logic rather than a programmed microcomputer.

The IPG 14 includes interface circuitry 104 for receiving signals from sensors and pace/sense electrodes located at specific sites of the patient's heart chambers and delivering cardiac pacing to control the patient's heart rhythm and resynchronize heart chamber activation. The interface circuitry 104 therefore includes a therapy delivery system 106 intended for delivering cardiac pacing impulses under the control of control and timing system 102. Delivery of pacing pulses to two or more heart chambers is controlled in part by the selection of programmable pacing intervals, which can include atrial-atrial (A-A), atrial-ventricular (A-V), and ventricular-ventricular (V-V) intervals.

Physiologic input signal processing circuit 108 is provided for receiving cardiac electrogram (EGM) signals for determining a patient's heart rhythm. Physiologic input signal processing circuit 108 additionally receives signals from left ventricular wall motion sensor 62, and optionally RV wall motion sensor 60, and processes these signals and provides signal data to control and timing system 102 for further signal analysis. For purposes of illustration of the possible uses of the invention, a set of lead connections are depicted for making electrical connections between the therapy delivery system 106 and the input signal processing circuit 108 and sets of pace/sense electrodes, wall motion sensors, and any other physiological sensors located in operative relation to the RA, LA, RV and LV.

Control and timing system 102 controls the delivery of bi-atrial, bi-ventricular, or multi-chamber cardiac pacing pulses at selected intervals intended to improve heart chamber synchrony. The delivery of pacing pulses by IPG 14 may be provided according to programmable pacing intervals, such as programmable conduction delay window times as generally disclosed in U.S. Pat. No. 6,070,101 issued to Struble et al., incorporated herein by reference in its entirety, or programmable coupling intervals as generally disclosed in above-cited U.S. Pat. No. 6,473,645 issued to Levine. Selection of the programmable pacing intervals is preferably based on a determination of left ventricular wall motion derived from sensor 62 signals as will be described in greater detail below.

The therapy delivery system 106 can optionally be configured to include circuitry for delivering cardioversion/defibrillation therapy in addition to cardiac pacing pulses for controlling a patient's heart rhythm. Accordingly, leads in communication with the patient's heart could additionally include high-voltage cardioversion or defibrillation shock electrodes.

A battery 136 provides a source of electrical energy to power components and circuitry of IPG 14 and provide electrical stimulation energy for delivering electrical impulses to the heart. The typical energy source is a high energy density, low voltage battery 136 coupled with a power supply/POR circuit 126 having power-on-reset (POR) capability. The power supply/POR circuit 126 provides one or more low voltage power (Vlo), the POR signal, one or more reference voltage (VREF) sources, current sources, an elective replacement indicator (ERI) signal, and, in the case of a cardioversion/defibrillator capabilities, high voltage power (Vhi) to the therapy delivery system 106. Not all of the conventional interconnections of these voltages and signals are shown in FIG. 2.

Current electronic multi-chamber pacemaker circuitry typically employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 2, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers included in microprocessor-based control and timing system 102 may be used for storing data compiled from sensed EGM signals, wall motion signals, and/or relating to device operating history or other sensed physiologic parameters for uplink telemetry transmission upon receipt of a retrieval or interrogation instruction via a downlink telemetry transmission. Criteria for triggering data storage can be programmed via down linked instructions and parameter values. Physiologic data, including wall motion data, may be stored on a triggered or periodic basis or by detection logic within the physiologic input signal processing circuit 108. In some cases, the IPG 14 includes a magnetic field sensitive switch 130 that closes in response to a magnetic field, and the closure causes a magnetic switch circuit 120 to issue a switch closed (SC) signal to control and timing system 102 which responds in a magnet mode. For example, the patient may be provided with a magnet 116 that can be applied over the subcutaneously implanted IPG 14 to close switch 130 and prompt the control and timing system to deliver a therapy and/or store physiologic data. Event related data, e.g., the date and time and current pacing parameters, may be stored along with the stored physiologic data for uplink telemetry in a later interrogation session.

Uplink and downlink telemetry capabilities are provided to enable communication with either a remotely located external medical device or a more proximal medical device on or in the patient's body. Stored EGM, or LV wall motion data as well as real-time generated physiologic data and non-physiologic data can be transmitted by uplink RF telemetry from the IPG 14 to the external programmer or other remote medical device 26 in response to a downlink telemetered interrogation command. As such, an antenna 128 is connected to radio frequency (RF) transceiver circuit 124 for the purposes of uplink/downlink telemetry operations. Telemetering both analog and digital data between antenna 128 and an external device 26, also equipped with an antenna 118, may be accomplished using numerous types of telemetry systems known in the art for use in implantable devices.

The physiologic input signal processing circuit 108 includes at least one electrical signal amplifier circuit for amplifying, processing and in some cases detecting sense events from characteristics of the electrical sense signal or sensor output signal. The physiologic input signal processing circuit 108 may thus include a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave or R-wave, respectively and providing an atrial sense or ventricular sense event signal to the control and timing system 102. Timing and control system 102 responds in accordance with its particular operating system to deliver or modify a pacing therapy, if appropriate, or to accumulate data for uplink telemetry transmission in a variety of ways known in the art. Thus the need for pacing pulse delivery is determined based on EGM signal input according to the particular operating mode in effect. The intervals at which pacing pulses are delivered are preferably determined based on an assessment of LV wall motion data.

As such, input signal processing circuit 108 further includes signal processing circuitry for receiving, amplifying, filtering, averaging, digitizing or otherwise processing the LV wall motion sensor signal. If additional wall motion sensors are included in the associated lead system, for example a RV wall motion sensor, additional wall motion signal processing circuitry may be provided as needed. Wall motion signal processing circuitry is further provided for detection and/or determination of one or more wall motion signal characteristics such as maximum and minimum peak amplitudes, slopes, integrals, or other time or frequency domain signal characteristics that may be used as indices of wall motion or correlates to hemodynamic performance. Such wall motion signal characteristic values determined from an LV wall motion sensor signal are made available to control and timing system 102 via LV MOTION signal line for use in algorithms performed for identifying pacing intervals producing optimal LV wall motion. If an RV wall motion sensor is present, an additional RV MOTION signal line provides RV wall motion signal data to control and timing system 102.

Figure 3:
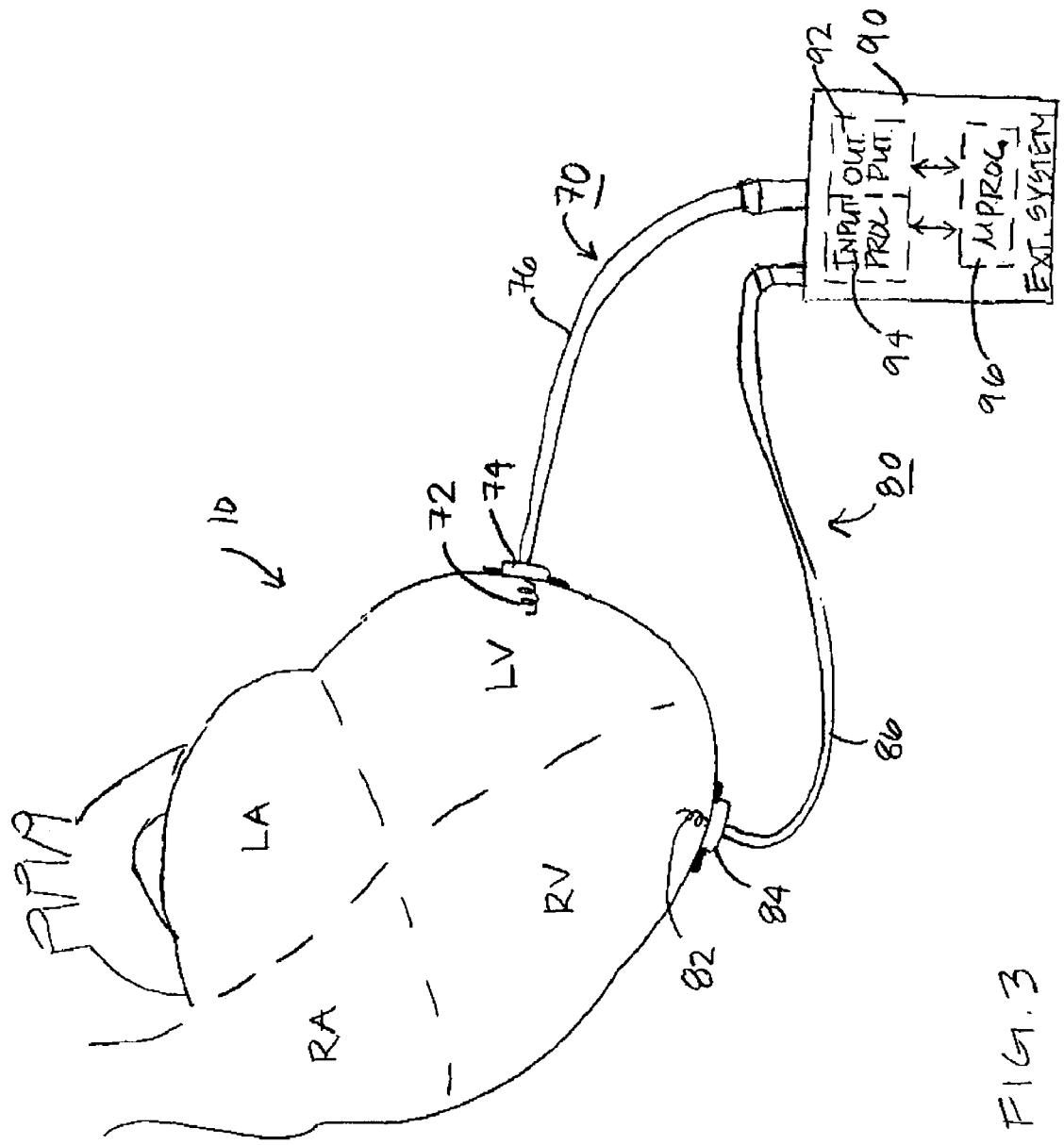
FIG. 3 depicts an alternative, epicardial lead system coupled to a patient's heart.

FIG. 3 depicts an alternative, epicardial lead system coupled to a patient's heart. Epicardial leads may be used in conjunction with either chronically implantable or temporary external pacing systems. In the embodiment shown, RV epicardial lead 80 is shown fixed via an active fixation electrode 82 near the apex of the RV such that the active fixation electrode 82 is positioned in contact with the RV epicardial tissue for pacing and sensing in the right ventricle. RV epicardial lead 80 may optionally be equipped with an RV wall motion sensor 84 for detecting motion or acceleration of the RV apical region. LV epicardial lead 70 is shown fixed via an active fixation electrode 72 in the LV free wall such that active fixation electrode 72 is positioned in contact with the LV epicardial tissue for pacing and sensing in the left ventricle. LV epicardial lead 70 is equipped with a wall motion sensor 74 for detecting motion or acceleration of the LV free wall. Epicardial lead systems may further include epicardial RA and/or LA leads. Various combinations of epicardial and transvenous endocardial leads are also possible for use with biventricular or multichamber cardiac stimulation systems.

In FIG. 3, RV and LV epicardial leads 70 and 80 are shown coupled to an external, temporary cardiac pacing device 90. External pacing device 90 is preferably a microprocessor controlled device including microprocessor 96 with associated RAM and ROM for storing and executing firmware and programmable software for controlling the delivery of pacing pulses to LV and RV pace/sense electrodes 72 and 82. External device 90 receives signals from and delivers electrical pulses to LV and RV pace/sense electrodes 72 and 82 via conductors included in LV epicardial lead body 76 and RV epicardial lead body 86. EGM signals, LV wall motion signals, and optionally RV wall motion signals are received as input to input signal processing circuitry 94. Pacing impulses are delivered by output circuitry 92 as needed, based on sensed EGM signals, at intervals determined based on signals received from LV wall motion sensor 74 as will be described in greater detail below. It is recognized that an epicardial lead system such as that shown in FIG. 3 that includes an LV wall motion sensor and optionally an RV wall motion sensor may alternatively be used in conjunction with an implantable pacing system, such as the multi-chamber system described above and shown in FIGS. 1 and 2.

External device 90 of FIG. 3 and implantable device 14 of FIGS. 1 and 2 are shown to provide both sensing/monitoring and pacing delivery capabilities. Certain device features may be enabled or disabled as desired. For example, monitoring of LV wall motion without delivery of a pacing therapy may be desired. LV wall motion sensor signal data may therefore be received, processed and stored by an implantable or external device for later analysis and review by a clinician.

Figure 4:
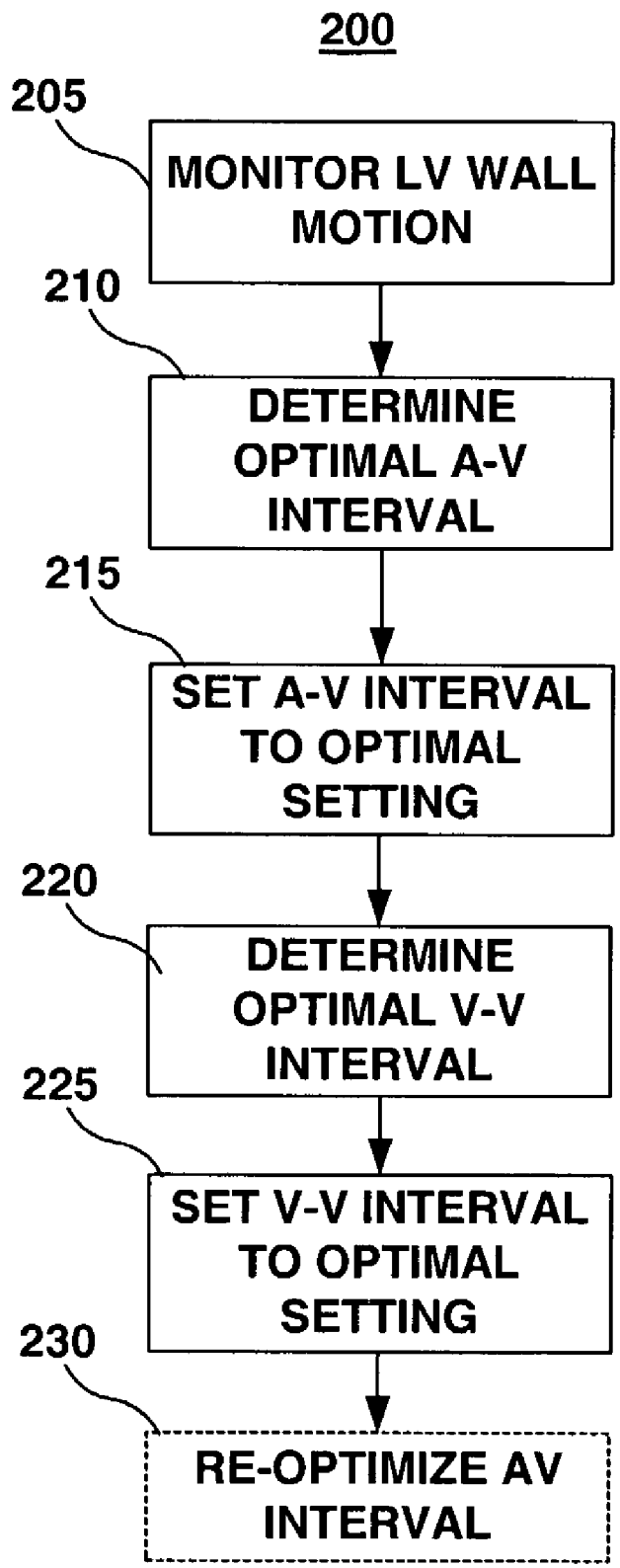
FIG. 4 is a flow chart providing an overview of a method for optimizing cardiac pacing intervals based on monitoring LV wall motion.

FIG. 4 is a flow chart providing an overview of a method for optimizing cardiac pacing intervals based on monitoring LV wall motion. Method 200 begins at step 205 by monitoring LV wall motion. Preferably a wall motion sensor is implanted in or proximate to the LV free wall as described above. More preferably, an LV wall motion signal is obtained from an accelerometer located on a coronary sinus lead advanced such that the accelerometer is positioned in a cardiac vein over the mid-lateral, mid-basal or basal segment of the left ventricular free wall.

At step 210, an optimal A-V interval is determined if the pacing mode is an atrioventricular or atrio-biventricular mode. Depending on the dual chamber or multichamber pacing system being used, a right A-V interval or a left A-V interval or both may be determined. For the embodiment shown in FIG. 1A, an optimal right atrial to right ventricle interval is determined. However, in other embodiments, the left atrial-left ventricular interval is optimized based on LV wall motion to ensure optimal filling of the LV. A method for determining an optimal A-V interval based on LV wall motion will be described in conjunction with FIG. 5. At step 215, the A-V interval is automatically adjusted to the optimal A-V interval determined at step 210.

At step 220, the optimal V-V interval is determined for bi-ventricular or atrio-biventricular pacing modes. A method for optimizing the V-V interval based on LV wall motion will be described in conjunction with FIG. 7. At step 225, the V-V interval is automatically adjusted to the optimal V-V interval determined at step 220. After adjusting the V-V interval, an optional step 230 may be performed to re-optimize the A-V interval. Verification of the provisionally determined optimal A-V interval is made by re-determining the optimal A-V interval during biventricular pacing at the newly optimized V-V interval. The A-V interval may be re-adjusted accordingly if a different A-V interval is identified as being optimal during pacing at the optimal V-V interval.

Figure 5:
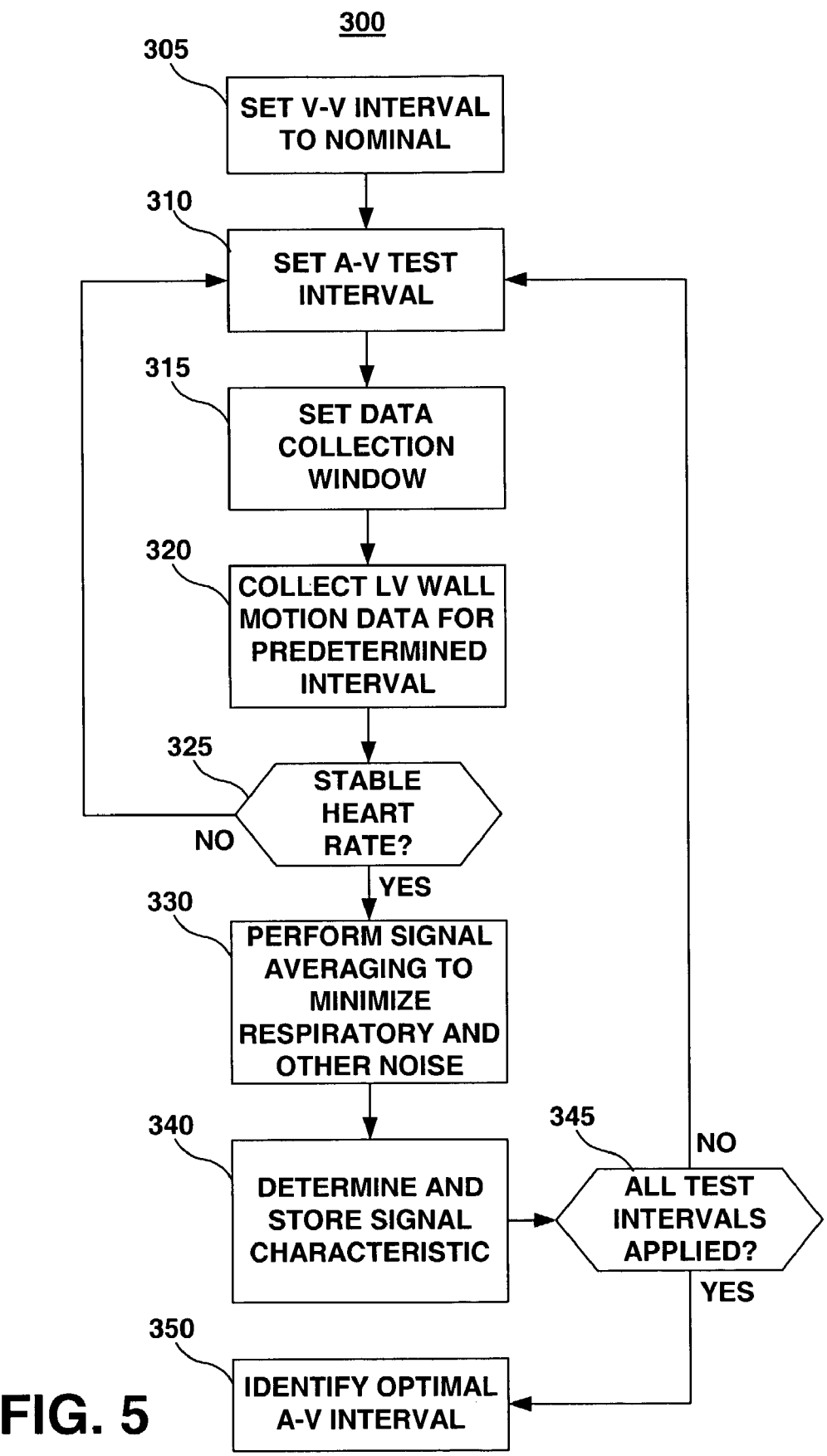
FIG. 5 is a flow chart summarizing steps included in a method for determining an optimal AV interval based on left ventricular wall motion for use in the method of FIG. 4.

FIG. 5 is a flow chart summarizing steps included in a method for determining an optimal AV interval based on left ventricular wall motion for use in method 200 of FIG. 4. Method 300 begins at step 305 by setting the V-V interval to a nominal setting, preferably to 0 ms such that the left and right ventricles are paced simultaneously. At step 310 an A-V test interval is set. A number of predetermined test A-V intervals may be programmed. In a patient with intact atrioventricular conduction, the A-V intervals tested may include the intrinsic A-V interval. In order to allow intrinsic A-V conduction, the A-V interval is set at a maximum setting or a setting longer than the intrinsic A-V conduction time. The intrinsic A-V conduction time may be determined by measuring the interval from an atrial pacing pulse to a subsequently sensed R-wave. Remaining test A-V intervals may be applied at decreasing increments from the intrinsic A-V interval. Alternatively, test A-V intervals may be applied randomly ranging from 0 ms to the intrinsic A-V interval. If atrioventricular conduction is not intact, a set of test A-V intervals may be selected over a predefined range, for example a range from 0 ms to on the order of 250 ms.

At step 315 a data collection window is set. LV wall motion data is preferably collected during systolic contraction such that acceleration or motion of the left ventricular wall segment over which the wall motion sensor is positioned may be measured. However, LV wall motion data may be acquired for use in assessing LV function or optimizing a therapy during the isovolumic contraction phase, the ejection phase, isovolumic relaxation, early diastolic filling, and/or late diastolic filling. The data collection window may be a fixed time interval following a delivered ventricular or atrial pacing pulse (or sensed R-wave if intrinsic A-V conduction is being tested in patients without AV block). A data collection window may be set as a time interval beginning at the delivery of a ventricular pacing pulse with a duration on the order of 30 to 180 ms, for example.

At step 320, the LV wall motion signal is sampled during the data collection window for each cardiac cycle during a predetermined time interval or for a predetermined number of cardiac cycles. In an alternative embodiment, the LV wall motion signal may be acquired continuously during the predetermined time interval or number of cardiac cycles and subsequently processed to separate components associated with the maximum acceleration phase of the systolic contraction. The time interval or number of cardiac cycles preferably extends over at least one respiration cycle such that averaging of the LV wall motion signal over a respiration cycle may be performed to eliminate variations in the LV wall motion measurements due to respiration. In one embodiment, the start and stop of wall motion data acquisition may be triggered by sensing a respiration cycle. Respiration may be detected based on impedance measurements or other methods known in the art.

At decision step 325, verification of a stable heart rate during the data acquisition interval is performed. Heart rate instability, such as the presence of ectopic heart beats or other irregularities, would produce anomalous LV wall motion data. As such, the heart rate preferably stays within a specified range. In one embodiment, heart rate stability may be verified by determining the average and standard deviation of the cardiac cycle length during the data acquisition period. The cardiac cycle length may be determined as the interval between consecutive ventricular events including ventricular pacing pulses and any sensed R-waves. If the average cardiac cycle length or its standard deviation falls outside a predefined range, the data is considered unreliable. Data acquisition may be repeated by returning to step 315 until reliable data is collected for the current test interval setting.

At step 330, signal averaging is performed to minimize the effects of respiration-related or other noise. The signals acquired during each cardiac cycle over the data collection interval are averaged to obtain an overall average LV wall motion signal. At step 340, one or more signal features are determined from the averaged signal as a measurement of LV wall motion and stored in device memory with corresponding test interval information. Preferably, the maximum amplitude of an accelerometer signal or its maximum excursion determined as the difference between the maximum and minimum peak amplitude, also referred to herein as "peak-to-peak difference" is determined as a measure of the maximum acceleration of the LV wall segment during systole. In one embodiment, the maximum peak amplitude or peak-to-peak difference of an accelerometer signal during isovolumic contraction is used as a metric of LV function. Other LV wall motion signal features may additionally or alternatively be determined as indices of LV mechanical function or hemodynamic correlates. Other LV wall motion signal features that may be derived include, but are not limited to, a slope, an integral, a frequency component, or other time or frequency domain characteristics.

If all test A-V intervals have not yet been applied, as determined at decision step 345, the method 300 returns to step 310 to adjust the A-V interval to the next test setting. Once all test A-V intervals have been applied, the optimal A-V interval is identified from the stored LV wall motion data at step 350.

Figure 6:
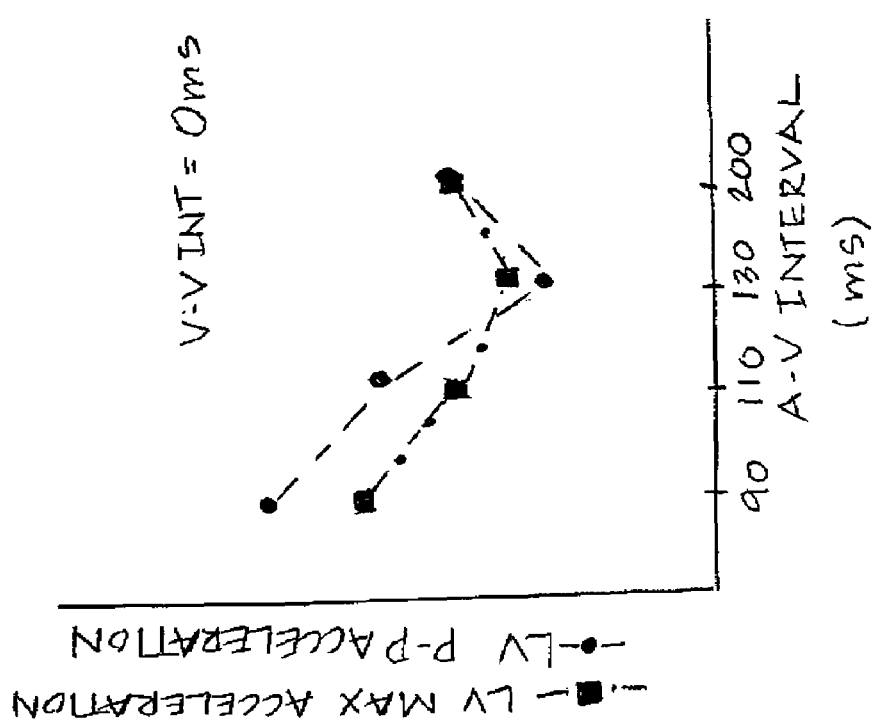
FIG. 6 is a graph of sample, experimental LV wall motion data collected from an accelerometer during atrio-biventricular pacing at varying A-V intervals and simultaneous right and left ventricular pacing (V-V interval set to 0 ms).

FIG. 6 is a graph of sample, experimental LV wall motion data collected from an accelerometer during atrio-biventricular pacing at varying A-V intervals and simultaneous right and left ventricular pacing (V-V interval set to 0 ms). As A-V interval is increased from 90 ms to 200 ms, the maximum LV acceleration and peak-to-peak acceleration decrease to a plateau point or "saddle point," then increase again. In one embodiment, the optimal A-V interval is selected as an A-V interval corresponding to the plateau or "saddle" point found by plotting a derived LV wall motion parameter as a function of A-V interval. In the example shown in FIG. 6, the derived parameter is the peak-to-peak difference of an accelerometer signal. Based on this parameter, and the criteria described above, an optimal A-V interval can be identified as 130 ms. Shorter A-V intervals can result in overlapping of left atrial and ventricular contraction and abrupt truncation of atrial contraction, resulting in an overall inefficient ejection of blood from the ventricles and mitral valve regurgitation. Longer A-V intervals are undesirable because of fusion between the atrial and ventricular filling phases of the cardiac cycle resulting in altered ventricular filling patterns. Reference is made to Leung S K et al., Pacing Clin Electrophysiol. 2000;23:1762-6.

When method 300 is executed by an external pacing system, LV wall motion data may be displayed in real-time or stored and presented following an optimization procedure. When method 300 for identifying an optimal A-V interval is executed by an implanted device, LV wall motion data may be stored for later uplinking to an external device for display and review by a physician. After identifying the optimal A-V interval, the A-V interval setting may be automatically adjusted according to method 200 described above.

Figure 7:
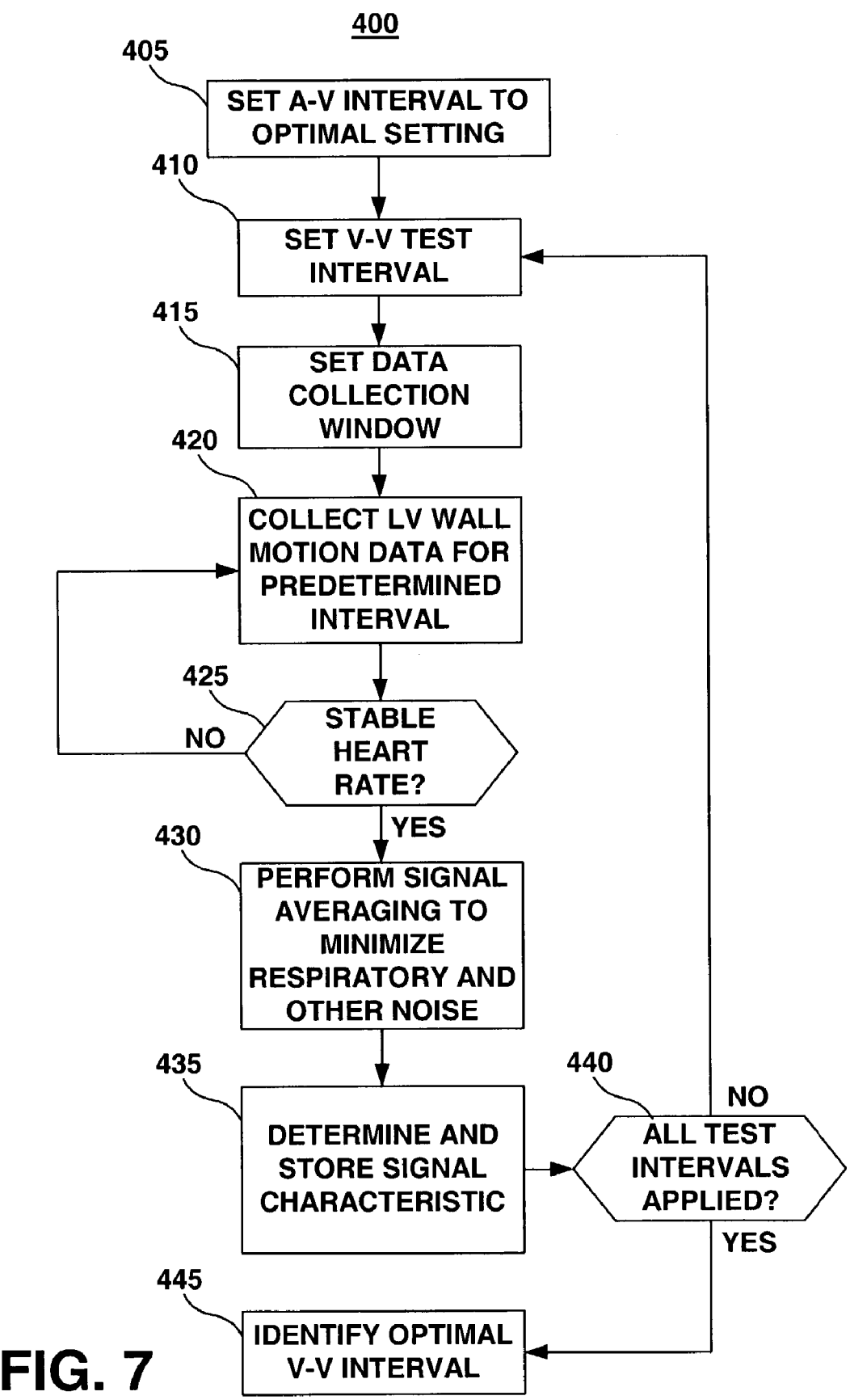
FIG. 7 is a flow chart summarizing steps included in a method for determining an optimal V-V interval based on left ventricular wall motion for use the method FIG. 4.

FIG. 7 is a flow chart summarizing steps included in a method for determining an optimal V-V interval based on left ventricular wall motion for use in method 200 of FIG. 4. At step 405, the A-V interval is programmed to an optimal setting determined according to method 300 of FIG. 4. At step 410, the V-V interval is set to a test interval. A range of test intervals are predefined and may be delivered in a random, generally increasing, or generally decreasing fashion. A range of test intervals may include intervals that result in the right ventricle being paced prior to the left ventricle and intervals that result in the left ventricle being paced prior to the right ventricle. A set of exemplary test intervals includes right ventricular pacing 20 ms and 40 ms prior to left ventricular pacing, simultaneous left and right ventricular pacing (a V-V interval of 0 ms), and left ventricular pacing 20 ms and 40 ms prior to the right ventricle.

Method 400 proceeds to determine the optimal V-V interval in a manner similar to method 300 for determining the optimal A-V interval described above. A data collection window is set at step 415, and LV wall motion data is collected for a predetermined time interval or number of cardiac cycles at step 420 during the data collection window applied to each cardiac cycle. After verifying a stable heart rate at step 425, signal averaging is performed at step 430 allowing an average peak amplitude or average peak-to-peak difference or other signal characteristic to be determined at step 435. After all test V-V intervals are applied as determined at decision step 440, the optimal V-V interval is identified at step 445.

Figure 8:
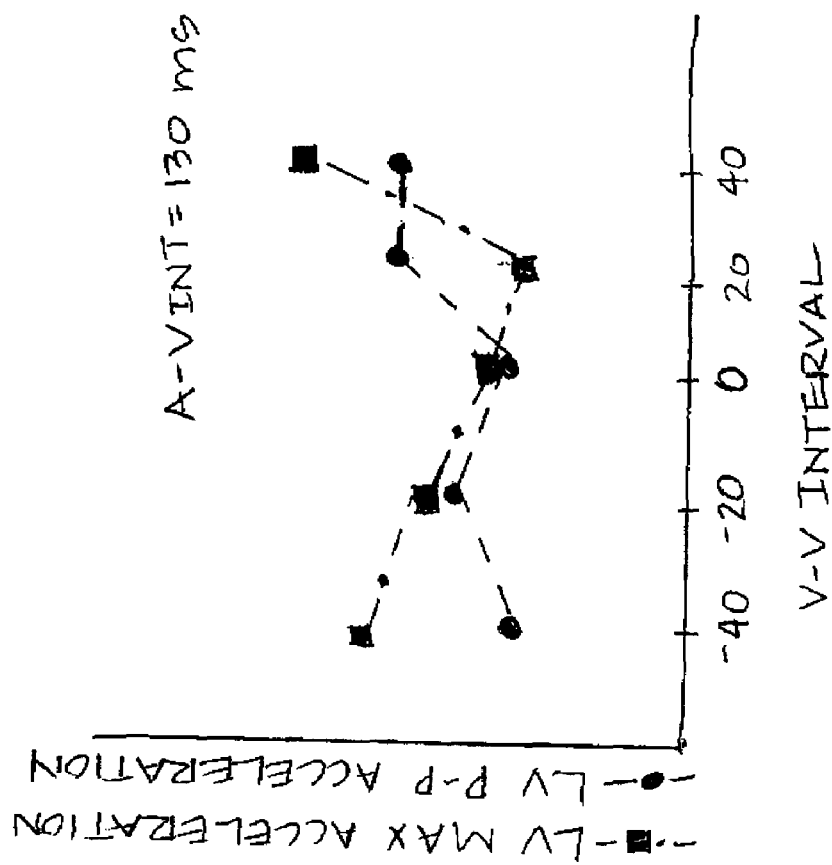
FIG. 8 is a graph of sample, experimental LV wall motion data collected from an accelerometer during atrio-biventricular pacing at varying V-V intervals and an A-V interval previously optimized to 130 ms.

FIG. 8 is a graph of sample, experimental LV wall motion data collected from an accelerometer during atrio-biventricular pacing at varying V-V intervals and an A-V interval previously optimized to 130 ms. Simultaneous right and left ventricular pacing occurs at a V-V interval of 0 ms. A convention of negative V-V intervals indicates the left ventricle is paced earlier than the right ventricle, and positive V-V intervals indicates right ventricular pacing occurs earlier than left ventricular pacing. In one embodiment, the optimal V-V interval is selected as the interval producing the maximum LV wall segment acceleration based on the maximum peak amplitude, peak-to-peak difference, or based on a fiducial point of an accelerometer signal. In the example shown, the optimal V-V interval may be identified, based on maximum LV acceleration, as a 40 ms interval with the right ventricle paced first and the left ventricle paced second.

When method 400 is executed by an external pacing system, LV wall motion data may be displayed in real-time or stored and presented following an optimization procedure. When method 400 for identifying an optimal V-V interval is executed by an implanted device, LV wall motion data may be stored for later uplinking to an external device for display and review by a physician. After identifying the optimal V-V interval, the V-V interval setting may be automatically adjusted according to method 200 described above.

As noted previously, after adjusting the V-V interval to an optimal setting, verification that the A-V interval is still optimal may be desired (step 230, FIG. 4). In order to re-optimize the A-V interval, method 300 may be performed as described above with the V-V interval programmed to the optimal setting identified by method 400 rather than a nominal setting. If a different A-V interval is found to be optimal, the A-V interval setting may be adjusted appropriately.

It is contemplated that optimization of A-V and V-V intervals based on LV wall motion according to the methods above may be performed in conjunction with an assessment of other wall segment motion, such as the RV apex. In particular, it may be desired to verify that other wall segment motion has not been degraded due to optimization of LV wall motion. It may also be desirable to optimize one or more pacing intervals based on LV wall motion and other pacing intervals based on RV apical wall motion or the motion of other wall segments.

Figure 9:
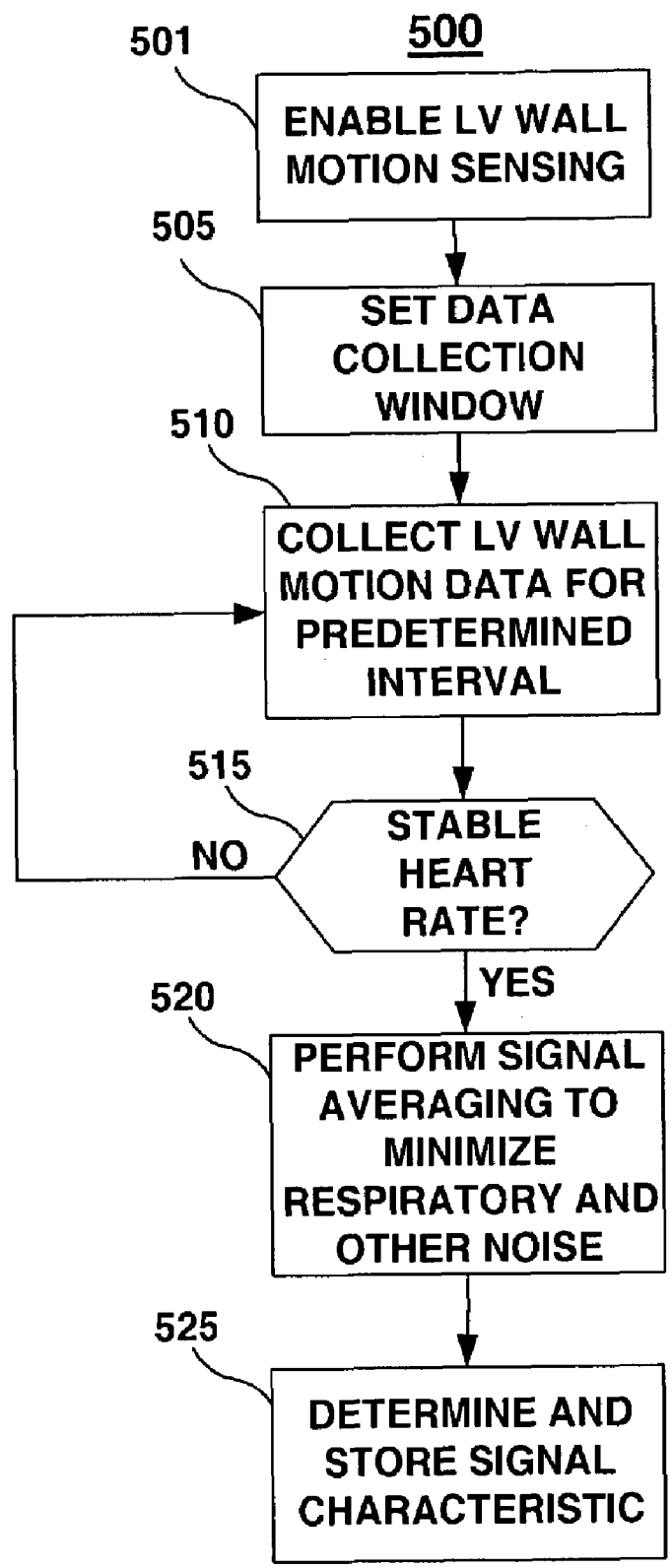
FIG. 9 is a flow chart summarizing steps included in a method for monitoring left ventricular function based on lateral wall motion.

FIG. 9 is a flow chart summarizing steps included in a method for monitoring left ventricular function based on lateral wall motion. As indicated previously, evaluation of left ventricular function is of interest for both diagnostic and therapeutic applications. Thus, it is recognized, that aspects of the present invention may be employed for monitoring purposes without optimization of a therapy delivery. As such, method 500 summarized in FIG. 9 may be implemented in an implantable or external device, such as the devices those shown in FIGS. 1A, 1B and FIG. 3, for monitoring LV function by deriving and storing an LV wall motion parameter from a sensed LV wall motion signal. The therapy delivery functions of such devices may be selectively disabled or, if enabled, the optimization of cardiac pacing intervals based on LV wall motion may be selectively enabled or disabled. Method 500 may alternatively be implemented in internal or external devices that do not include therapy delivery capabilities, but in association with an LV lead equipped with a wall motion sensor, are capable of processing and storing LV wall motion data.

LV wall motion may be sensed during a selected phase of the cardiac cycle on a continuous, periodic or triggered basis with the wall motion signal characteristic determined and stored after each predetermined interval of time or number of cardiac or respiratory cycles. For example, LV function may be evaluated on a periodic basis such as hourly, daily, weekly, or otherwise. Additionally or alternatively, LV function may be evaluated on a triggered basis, which may be a manual or automatic trigger. Automatic triggers may be designed to occur upon the detection of predetermined conditions during which LV function evaluation is desired, such as a particular heart rate range, activity, or other conditions.

In one embodiment, LV wall motion is monitored continuously and storage of LV wall motion data is triggered upon the detection of predetermined data storage conditions, such as, but not limited to, a heart rate, activity, or a condition relating to LV wall motion. For example, LV wall motion may be sensed continuously, and, if an LV wall motion parameter crosses a threshold or satisfies other predetermined data storage criteria, LV wall motion parameter(s) are stored.

Manual triggers for LV wall motion sensing and/or data storage may be delivered by a clinician or by a patient, for example when the patient feels symptomatic. Methods for manually triggering the storage of physiological data in an implantable device are generally described in U.S. Pat. No. 5,987,352 issued to Klein, et al., hereby incorporated herein by reference in its entirety.

Method 500 begins at step 501 when LV wall motion sensing is enabled according to the mode of operation of the monitoring device, which as just described, may be continuous, periodic, automatically- and/or manually-triggered monitoring. At step 505, an LV wall motion data collection window is set as described previously. At step 510, LV wall motion data is acquired for a predetermined interval of time or number of cardiac or respiratory cycles. At step 515, heart rate stability is verified as described previously. The wall motion signal is averaged over the number of cardiac cycles collected at step 520 to minimize respiratory or other noise. At step 525, a characteristic of the averaged signal is determined and stored as an indication of LV function. Other physiologic or parametric data may be stored with the LV function data such as heart rate, date and time of day, pacing modality and parameters, and/or any other physiological data that may be sensed by the monitoring device such as patient activity, blood pressure, etc.

When method 500 is implemented in an implantable device, stored data are available through uplink telemetry to an external device for later display and review by a physician. When method 500 is implemented in an external device, a display of LV function data may be updated each time an LV wall motion signal characteristic is determined.

Thus a method and apparatus have been described for monitoring left ventricular cardiac contractility and optimizing a cardiac therapy based on left ventricular lateral wall acceleration measured using a left ventricular lead equipped with an acceleration sensor. The methods described herein may advantageously be applied in numerous cardiac monitoring or therapy modalities including chronic or acute applications associated with implantable or external devices.

As is known in the art, besides the transducers described hereinabove, other types of transducers may be used provided, in general, that such transducers are hermetically sealed, are fabricated (on least on the exterior surfaces) of substantially biocompatible materials and appropriately dimensioned for a given application. With respect to appropriate dimension, a transducer intended to transvenous deployment should be susceptible of catheter or over-the-wire delivery. Thus, the radial dimension should be on the order of less than about 11 French and preferably about less than eight French. Also, the transducer should be somewhat supple, and not too long, in the longitudinal dimension so that the transducer can safely navigate the venous system, pass through the coronary sinus and enter vessels branching from the coronary sinus (e.g., the great cardiac vein, and the like). These dimensions can be relaxed for a transducer intended for deployment though a portion of the chest (e.g., a thoracotomy) with an affixation mechanism adapted to mechanically couple adjacent the lateral wall. Two adjacent locations include the epicardium and the pericardium. The dimensions may be relaxed to a greater extent if the epicardial receives the transducer, and to a lesser extent, to a portion of the pericardium. As is well known, the pericardium is the membranous sac filled with serous fluid that encloses the heart and the roots of the aorta and other large blood vessels. One example of appropriate fixation apparatus for epicedial application is a helical tipped lead that is screwed into the surface of the epicardium. For pericardial fixation a sealing member (e.g., compressible gasket or opposing members on each side of the pericardial sac) may be used in addition to an active fixation member such as a helical tipped lead.

As is also known in the art related to sensors and transducers, accelerometers can be described as two transducers, a primary transducer (typically a single-degree-of-freedom vibrating mass which converts the acceleration into a displacement), and a secondary transducer that converts the displacement (of a seismic mass) into an electric signal. Most accelerometers use a piezoelectric element as a secondary transducer. Piezoelectric devices, when subjected to a strain, output a voltage proportional to the strain, although piezoelectric elements cannot provide a signal under static (e.g., constant acceleration) conditions. Important characteristics of accelerometers include range of acceleration, frequency response, transverse sensitivity (i.e. sensitivity to motion in the non-active direction), mounting errors, temperature and acoustic noise sensitivity, and mass.

One type of primary transducer, which describe the internal mechanism of the accelerometer, include spring-retained seismic mass. In most accelerometers, acceleration forces a damped seismic mass that is restrained by a spring, so that it moves relative to the casing along a single axis. The secondary transducer then responds to the displacement and/or force associated with the seismic mass. The displacement of the mass and the extension of the spring are proportional to the acceleration only when the oscillation is below the natural frequency. Another accelerometer type uses a double-cantilever beam as a primary transducer which can be modeled as a spring-mass-dashpot, only the seismic mass primary transducer will be discussed.

Types of secondary transducers, which describe how the electric signal is generated from mechanical displacement, include: piezoelectric, potentiometric, reluctive, servo, strain gauge, capacitive, vibrating element, etc. These are briefly described as an introduction for the uninitiated.

Piezoelectric transducers are often used in vibration-sensing accelerometers, and sometimes in shock-sensing devices. The piezoelectric crystals (e.g., often quartz or ceramic) produce an electric charge when a force is exerted by the seismic mass under some acceleration. The quartz plates (two or more) are preloaded so that a positive or negative change in the applied force on the crystals results in a change in the electric charge. Although the sensitivity of piezoelectric accelerometers is relatively low compared with other types of accelerometers, they have the highest range (up to 100,000 g's) and frequency response (over 20 kHz).

Potentiometric accelerometers utilize the displacement of the spring-mass system linked mechanically to a wiper arm, which moves along a potentiometer. The system can use gas, viscous, magnetic-fluid, or magnetic damping to minimize acoustic noise caused by contact resistance of the wiper arm. Potentiometric accelerometers typically have a frequency range from zero to 20-60 Hz, depending on the stiffness of the spring, and have a high-level output signal. They also have a lower frequency response than most other accelerometers, usually between 15-30 Hz.

Reluctive accelerometers use an inductance bridge, similar to that of a linear variable differential transducer to produce an output voltage proportional to the movement of the seismic mass. The displacement of the seismic mass in inductance-bridge accelerometers causes the inductances of two coils to vary in opposing directions. The coils act as two arms of an inductance bridge, with resistors as the other two arms. The AC output voltage of the bridge varies with applied acceleration. A demodulator can be used to convert the AC signal to DC. An oscillator can be used to generate the required AC current when a DC power supply is used, as long as the frequency of the AC signal is far greater than that of the frequency of the acceleration.

In servo accelerometers, acceleration causes a seismic mass "pendulum" to move. When motion is detected by a position-sensing device, a signal is produced that acts as the error signal in the closed-loop servo system. After the signal has been demodulated and amplified to remove the steady-state component, the signal is passed through a passive damping network and is applied to a torquing coil located at the axis of rotation of the mass. The torque developed by the torquing coil is proportional to the current applied, and counteracts the torque acting on the seismic mass due to the acceleration, preventing further motion of the mass. Therefore, the current through the torquing coil is proportional to acceleration. This device can also be used to measure angular acceleration as long as the seismic mass is balanced. Servo accelerometers provide high accuracy and a high-level output at a relatively high cost, and can be used for very low measuring ranges (well below 1 g).

Strain gauge accelerometers, often called "piezoresistive" accelerometers, use strain gauges acting as arms of a Wheatstone bridge to convert mechanical strain to a DC output voltage. The gauges are either mounted to the spring, or between the seismic mass and the stationary frame. The strain gauge windings contribute to the spring action and are stressed (i.e., two in tension, two in compression), and a DC output voltage is generated by the four arms of the bridge that is proportional to the applied acceleration.

These accelerometers can be made more sensitive with the use of semiconductor gauges and stiffer springs, yielding higher frequency response and output signal amplitude. Unlike other types of accelerometers, strain gauge accelerometers respond to steady-state accelerations.

In a capactivie accelerometer a change in acceleration causes a change in the space between the moving and fixed electrodes of a capacitive accelerometer. The moving electrode is typically a diaphragm-supported seismic mass or a flexure-supported, disk-shaped seismic mass. The element can act as the capacitor in the LC or RC portion of an oscillator circuit. The resulting output frequency is proportional to the applied acceleration.

In a vibrating element accelerometer, a very small displacement of the seismic mass varies the tension of a tungsten wire in a permanent magnetic field. A current through the wire in the presence of the magnetic field causes the wire to vibrate at its resonant frequency (like a guitar string). The circuitry then outputs a frequency modulation (deviation from a center frequency) that is proportional to the applied acceleration. Although the precision of such a device is high, it is quite sensitive to temperature variations and is relatively expensive.

Thus, those of skill in the art will recognize that while the present invention has been described herein in the context of specific embodiments, it is recognized that numerous variations of these embodiments may be employed without departing from the scope of the present invention. The descriptions provided herein are thus intended to be exemplary, not limiting, with regard to the following claims.

The invention claimed is:

1. A method for monitoring left ventricular function during delivery of a cardiac resynchronization therapy (CRT), comprising:
  deploying a motion sensor to a fixed location on a portion of a left ventricular lateral wall wherein the motion sensor generates a motion signal proportional to motion of the portion of the left ventricular lateral wall;
  opening a data collection window during a portion of a selected cardiac cycle phase;

storing the motion signal throughout at least a part of the portion of the data collection window for a predetermined time interval or for more than one cardiac cycle;

verifying a heart rate stability characteristic during the predetermined time interval or for more than one cardiac cycle averaging the stored motion signal; determining a signal characteristic from the averaged stored signal that is representative of left ventricular function; and delivering a cardiac resynchronization therapy (CRT) based at least in part upon the signal characteristic;

wherein the motion sensor consists of one from the group: a piezoelectric sensor, an optical sensor, a Hall-effect type sensor, a capacitive sensor, a resistive sensor, an inductive sensor.

2. A method according to claim 1, wherein said motion sensor is adapted to be disposed in a portion of the coronary sinus vessel or a blood vessel fluidly coupled to said coronary sinus.

3. A method according to claim 1, wherein said motion sensor is adapted to be disposed adjacent to a portion of the epicardium of the left ventricle of the heart.

4. A method according to claim 3, wherein the portion of the lateral wall is a basal portion of the lateral wall.

5. A method according to claim 4, wherein the portion of the lateral wall is a mid-basal portion of the lateral wall.

6. A method according to claim 1, wherein said motion sensor is adapted to be disposed within the pericardium of the heart.

7. A method according to claim 1, wherein said motion sensor is operatively coupled to an implantable medical device (IMD) and said IMD operatively couples to a first pacing electrode and a second pacing electrode.

8. A method according to claim 7, wherein the first pacing electrode or the second pacing electrode further comprises a sense electrode in electrical communication with a sensing circuit coupled to the IMD.

9. A method according to claim 7, wherein the first pacing electrode or the second pacing electrode comprises a sense electrode in electrical communication with a sensing circuit coupled to the IMD.

10. A method for optimizing cardiac pacing intervals based on left ventricular function for delivery of a cardiac resynchronization therapy (CRT), comprising;

placing a motion sensor into operative mechanical communication with a portion of a left ventricular lateral free wall so that the motion sensor generates a motion signal proportional to the motion of the left ventricular lateral free wall;

enabling a temporal data collection window corresponding to a selected cardiac cycle phase;

applying a cardiac pacing stimulus delivered according to a preselected set of test pacing parameters;

sensing the motion signal during at least a part of the temporal data collection window or during a more than one cardiac cycle for at least some members of the preselected set of test pacing parameters;

verifying a heart rate stability characteristic;

averaging the motion signal for the at least some members of the preselected set of test pacing parameters;

determining a signal characteristic from the averaged sensed signal that is representative of relatively improved left ventricular function during each of the selected test pacing parameters;

storing a cardiac pacing timing parameter for a right ventricular pacing electrode and for a left ventricular pacing electrode that resulted in the relatively improved left ventricular function;

delivering a cardiac resynchronization therapy (CRT) based upon the cardiac pacing timing parameter, wherein the motion sensor consists of one from the group; a piezoelectric sensor, an optical sensor, a Hall-effect type sensor, a capacitive sensor, a resistive sensor, an inductive sensor.

11. A method for monitoring left ventricular function during delivery of a cardiac resynchronization therapy (CRT), comprising:

deploying a motion sensor to a portion of a left ventricular lateral wall of a patient's heart, wherein the motion sensor generates motion signals proportional to motion of the portion of the left ventricular lateral wall and indicative of left ventricular function;

storing the motion signals throughout at least portions of a plurality of cardiac cycles;

verifying a heart rate stability characteristic during the plurality of cardiac cycles;

determining a signal characteristic from the stored motion signals that is representative of left ventricular function; and dependant upon the verified heart rate stability characteristic, delivering a cardiac resynchronization therapy (CRT) based upon the signal characteristic to optimize left ventricular function.

12. A method according to claim 11, wherein said motion sensor is deployed in a portion of a coronary sinus vessel or a blood vessel fluidly coupled to said coronary sinus.

13. A method according to claim 11, wherein said motion sensor is deployed adjacent to a portion of the epicardium of the left ventricle of the heart.

14. A method according to claim 11, wherein said motion sensor is deployed within the pericardium of the patient's heart.

15. A method according to claim 11, wherein said motion sensor is operatively coupled to an implantable medical device (IMD) and said IMD operatively couples to a first pacing electrode and a second pacing electrode.

16. A method for optimizing cardiac pacing intervals based on left ventricular function for delivery of a cardiac resynchronization therapy (CRT) of a patient's heart, comprising;

placing a motion sensor into operative mechanical communication with a portion of a left ventricular lateral free wall of the patient's heart so that the motion sensor generates motion signals proportional to the motion of the left ventricular lateral free wall and indicative of left ventricular function;

applying cardiac pacing stimuli delivered according to a preselected set of test pacing parameters;

sensing the motion signal during at least a part of a plurality of cardiac cycles for at least some members of the preselected set of test pacing parameters;

verifying a heart rate stability characteristic;

determining a signal characteristic from the sensed signals that is representative of relatively improved left ventricular function during each of the selected test pacing parameters;

storing a cardiac pacing parameter that resulted in the relatively improved left ventricular function; and dependant upon the verified heart rate stability characteristic, delivering a cardiac resynchronization therapy (CRT) based upon the stored cardiac pacing parameter.

17. A method according to claim 16, wherein said motion sensor is deployed in a portion of a coronary sinus vessel or a blood vessel fluidly coupled to said coronary sinus.

18. A method according to claim 16, wherein said motion sensor is deployed adjacent to a portion of the epicardium of the left ventricle of the heart.

19. A method according to claim 16, wherein said motion sensor is deployed within the pericardium of the patient's heart.

20. A method according to claim 16, wherein said motion sensor is operatively coupled to an implantable medical device (IMD) and said IMD operatively couples to a first pacing electrode and a second pacing electrode.

21. A method according to claim 20, wherein the first pacing electrode or the second pacing electrode comprises a sense electrode in electrical communication with a sensing circuit coupled to the IMD.

* * * * *

UNITED STATES PATENT AND TRADEMARK OFFICE
CERTIFICATE OF CORRECTION

PATENT NO. : 7,610,088 B2 Page 1 of 1
APPLICATION NO. : 10/376981
DATED : October 27, 2009
INVENTOR(S) : Edward Chinchoy It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 663 days.

Signed and Sealed this

Twelfth Day of October, 2010

David J. Kappos
*Director of the United States Patent and Trademark Office*